United States Patent [19]

Ginn et al.

[11] Patent Number: 5,443,457

[45] Date of Patent: Aug. 22, 1995

[54] TRACKING TIP FOR A SHORT LUMEN RAPID EXCHANGE CATHETER

[75] Inventors: Richard S. Ginn, San Jose; Stephen M. Salmon, Sunnyvale, both of Calif.

[73] Assignee: Cardiovascular Imaging Systems, Incorporated, Sunnyvale, Calif.

[21] Appl. No.: 201,101

[22] Filed: Feb. 24, 1994

[51] Int. Cl.[6] ............................................. A61M 25/00
[52] U.S. Cl. .............................. 604/280; 128/662.06; 604/53
[58] Field of Search ................ 604/96, 101, 102, 264, 604/280, 53; 606/192, 194; 128/662.06, 663.01

[56] References Cited

U.S. PATENT DOCUMENTS

| | | | |
|---|---|---|---|
| 4,552,554 | 11/1985 | Gould et al. | 604/51 |
| 4,748,982 | 6/1988 | Horzewski et al. | 606/192 |
| 4,762,129 | 7/1991 | Bonzel | 606/194 |
| 4,824,435 | 4/1989 | Giesy et al. | 604/49 |
| 4,932,413 | 6/1990 | Shockey et al. | 128/657 |
| 4,951,677 | 8/1990 | Crowley et al. | 128/662.6 |
| 5,024,234 | 6/1991 | Leary et al. | 128/663.1 |
| 5,180,367 | 1/1993 | Kontos et al. | 604/101 |
| 5,201,316 | 4/1993 | Pomeranz et al. | 128/662.6 |
| 5,203,338 | 4/1993 | Jang | 128/662.6 |
| 5,295,962 | 3/1994 | Crocker et al. | 604/101 |

OTHER PUBLICATIONS

Brochure—Product Development Update, InterTherapy, Fall 1990.

*Primary Examiner*—Corrine Maglione
*Attorney, Agent, or Firm*—Townsend and Townsend Khourie and Crew

[57] ABSTRACT

A catheter system includes a catheter sheath and a flexible working shaft within a working lumen of the sheath. The sheath includes a monorail-type guidewire lumen at its distal end, and a stiffening member is provided adjacent a side port of the monorail guidewire lumen to inhibit prolapse of the catheter as it is introduced past a bend or curve over a guidewire. In a first embodiment, the stiffening member may be secured directly within a working lumen of the catheter body. In a second embodiment, the stiffening member may be attached to a distal end of the working shaft, typically an imaging core.

26 Claims, 3 Drawing Sheets

TRACKING TIP FOR A SHORT LUMEN RAPID EXCHANGE CATHETER

BACKGROUND OF THE INVENTION

1. Field of the Invention

The present invention relates generally to the construction and use of vascular catheters and more particularly to systems and methods for exchanging vascular catheters having internal work elements over guidewires.

Atherosclerosis is a common human ailment arising from the deposition of fatty-like substances, referred to as atheroma or plaque, on the walls of blood vessels. Such deposits occur both in the peripheral blood vessels, which feed the limbs of the body, and the coronary vessels, which feed the heart. When deposits accumulate in localized regions of a blood vessel, narrowing of the vascular lumen, referred to as stenosis, occurs. Blood flow is restricted and the person's health is at serious risk.

Numerous approaches for opening such stenosed regions are known, including balloon angioplasty, where a balloon-tipped catheter is used to dilate a stenosed region (optionally in combination with a stent for maintaining patency); atherectomy, where a blade, cutting element, or other abrasive element, is used to remove the atheroma or plaque; spark gap reduction, where an electric spark burns through the atheroma or plaque; and laser angioplasty, where laser energy is used to ablate at least a portion of the atheroma or plaque. In order to facilitate treatment of the stenosis with any of these approaches, it is often desirable to obtain an image of the interior of the blood vessel at the region to be treated. Catheters having imaging elements such as ultrasonic transducers are now gaining widespread acceptance for producing such images.

Of particular interest to the present invention, ultrasonic imaging catheters will often include an imaging core comprising ultrasonic imaging transducer or reflective element mounted on a rotatable drive shaft disposed within a flexible catheter body. The transducer, reflective element or both, can be rotated within the catheter body to direct an ultrasonic signal generally outward in order to scan the interior of the blood vessel wall. High resolution images revealing information concerning the extent and nature of the stenotic material can thus be produced.

During diagnostic, imaging, and interventional vascular procedures, it is often desirable to "exchange" one catheter for another. By "exchange" it is meant that one catheter is withdrawn from the vascular system and the another catheter is introduced to the vascular system. In order to maintain distal access, the exchange will usually be performed over a guidewire which is left in place to facilitate both catheter withdrawal and reintroduction of the new catheter.

Because of their excessive lengths, typically over 100 cm, the exchange of one catheter for another over a guidewire can be a complex procedure. In the early days of angioplasty and other vascular procedures, guidewire lumens were provided over the entire length of the interventional or other catheter. Thus, to permit withdrawal of the catheter over a guidewire which remains in place within the vascular system, the guidewire would have to be generally twice as long as the catheter (in order to allow the user to hold onto a proximal portion of the guidewire as the catheter is introduced thereover). In an effort to simplify catheter exchange, and in particular to reduce the necessary length of the guidewire, specialized catheter designs have been developed.

Such specialized catheter designs are now commonly referred to as "rapid exchange" designs, where the guidewire lumen does not extend the full length of the interventional or other catheter, but rather extends only from the distal tip to a side port which terminates a short distance proximally of the distal tip. In the case of long lumen rapid exchange catheters, the side port for the guidewire will typically be 10 cm or more from the distal tip of the catheter. Thus, the distal end of the catheter which enters the most tortuous regions of the vasculature will usually be reinforced by the internal guidewire (which engages the catheter over the entire length of the catheter which lies within the coronary arteries), preventing buckling and prolapse. The extended length of the guidewire lumen, however, generally requires that the distal dimensions of the catheter be increased to accommodate both the guidewire and the interventional or imaging component of the catheter.

Short lumen rapid exchange catheter designs (often referred to as "monorail" designs) generally employ a much shorter guidewire lumen at the distal end of the catheter, typically in the range from about 1 cm to 4 cm. The interventional, imaging, or diagnostic component of the catheter may then be disposed proximally up the guidewire lumen, allowing a reduction in the cross-sectional area of the catheter.

While such short lumen rapid exchange designs have proven to be very valuable, particularly for introduction of catheters to very small blood vessels, the provision of a side port so close to the distal end of the catheter can mechanically compromise the catheter. This is a particular problem where the catheter carries a relatively stiff internal component, such as an ultrasonic imaging core, proximal to the guidewire side port. The location of the weakened side port immediately distal to the imaging core will frequently cause the catheter to kink or prolapse as it passes over the guidewire through a relatively tight bend or curve in the vasculature.

For these reasons, it would be desirable to provide catheter systems and catheter sheaths for use with internal work elements, such as imaging cores, which have a short lumen rapid exchange design for receiving guidewires but which are resistant to kinking or prolapse when introduced through tortuous regions of the blood vessels. It would be particularly desirable if such catheter systems and sheaths were reinforced in the region of the guidewire side port in such a way that the cross-sectional area of the guidewire is not increased and the ability to introduce the catheter sheath or system over a guidewire is not compromised. Such catheter systems and sheaths should be compatible with catheters having internal work elements, particularly internal imaging cores, so that combinations of the catheter sheath and internal work element can be introduced simultaneously over the guidewire to a target location within the vascular system.

2. Description of the Background Art

Vascular ultrasonic imaging catheters having rapid exchange designs are described in U.S. Pat. Nos. 5,201,316; 5,024,234; and 4,951,677 (FIGS. 17 and 17A). Catheter sheaths having guidewire side ports near their distal ends are described in U.S. Pat. Nos. 4,932,413; 4,824,435; and 4,552,554. A short lumen rapid exchange balloon dilatation catheter is described in U.S. Pat. No. 4,762,129. An ultrasonic imaging catheter having a common distal lumen and rapid exchange capability is described in U.S. Pat. No. 5,203,338. A monorail sheath catheter usable with an ultrasonic imaging core was described in a Product Development Update of InterTherapy, Costa Mesa, Calif., dated Fall 1990.

SUMMARY OF THE INVENTION

According the present invention, a catheter system comprises a catheter sheath and a flexible working shaft. The catheter sheath includes a tubular body having a proximal end, a distal end, a working lumen, and a guidewire lumen. The flexible working shaft is disposed within the working lumen and includes a working element at or near its distal end. The guidewire lumen extends from the distal end of the shaft to a side port located a short proximal distance from the distal end to define a "short lumen rapid exchange" catheter design. Typically, the side port will be located from 1 cm to 10 cm from the distal tip of the catheter, usually from 1 cm to 5 cm from the distal tip. Prolapse of the catheter at the side port is inhibited by a stiffening member disposed adjacent to the side port, usually within the working lumen.

In a first embodiment of the present invention, the stiffening member is fixedly secured to the catheter body, usually within the working lumen opposite to the side port of the guidewire lumen. In a preferred aspect of the first embodiment, the stiffening member will comprise a polymeric wedge which isolates the guidewire lumen from the working lumen. In an alternative embodiment, the stiffening member will comprise a resilient element, such as a metal coil, which is disposed along the inner wall of the working lumen.

In a second embodiment of the present invention, the stiffening member is attached to a distal end of the working shaft and is disposed distally of the working element. The stiffening member is usually in the form of a metal coil attached to a distal end of the working element and will be disposed within a distal portion of the working lumen when the working shaft is present therein. By properly aligning the working element so that the stiffening member is disposed adjacent the side port, the stiffening member will act to reinforce and prevent prolapse of the catheter sheath as it is being introduced through bends and branches in the vasculature.

The present invention further comprises the catheter sheath itself comprising a tubular body and stiffening member fixedly secured within the distal end adjacent the side port.

The present invention still further comprises an improved method for introducing an ultrasonic imaging catheter to a blood vessel over a guidewire, where the improvement comprises selectively stiffening the catheter adjacent to a side port which receives the guidewire in a monorail fashion. Such stiffening prevents prolapse of the catheter at the region of the side port. In a first aspect, the catheter is stiffened by a member which is fixedly secured within the catheter adjacent the side port. In a second aspect, the catheter is stiffened by a stiffening member which is secured to a distal end of an imaging core comprising an ultrasonic imaging element attached to a flexible shaft.

DESCRIPTION OF THE PREFERRED EMBODIMENT

Figure 1:
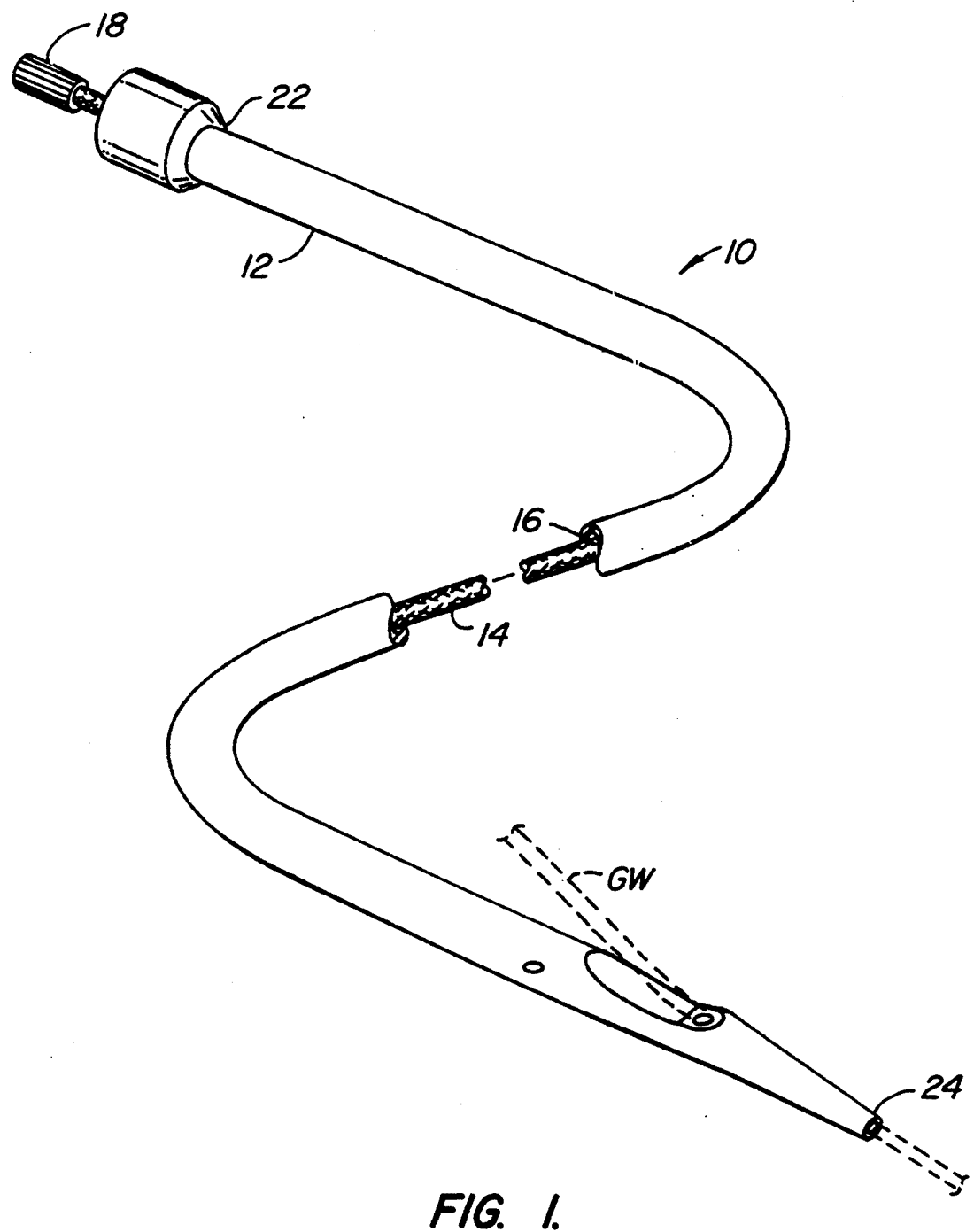
FIG. 1 is a perspective view of a catheter system constructed in accordance with the principles of the present invention.

Catheter systems according to the present invention comprise catheter sheaths which receive a working shaft having a working element at or near its distal end. The work element will usually be an ultrasonic transducer useful for intravascular imaging, but may also comprise a variety of other diagnostic or interventional elements such as cutting elements, abrasive heads, and the like. The following discussion will be directed at the case where the working shaft comprises an ultrasonic imaging core including a flexible drive cable having an ultrasonic imaging element at its distal end. Optionally, the ultrasonic imaging transducer may be mounted in tandem with a mirror for reflecting the ultrasonic signal laterally in order to image a region surrounding the catheter sheath as the imaging core is rotated. The construction and use of such ultrasonic imaging cores is now well known and well described in the patent and medical literature.

Catheter sheaths of the present invention will comprise a tubular body having proximal and distal ends and at least one lumen extending between said ends. The tube will usually be formed by extrusion of an organic polymer, typically a thermoplastic such as polyethylene, polyethyleneterephthalate (PET), polyurethane, polyvinylchloride (PVC), nylon, and the like. The tubes will usually be unreinforced, but optionally may be reinforced with metal wires, metal braided cables, metal coils, and the like. The catheter body will typically have a length in the range from about 60 cm to 200 cm, usually being from 60 cm to 110 cm for use in the peripheral arteries and from 90 cm to 150 cm for use in the coronary arteries. The diameter will usually be 1 French (F=0.33 mm) or larger, more usually being from 2 F to 9 F. The catheter constructions of the present invention are particularly useful with very small diameter catheters below 6 F, particularly below 4 F.

The catheter sheath will have both a working lumen and a guidewire lumen, where the guidewire lumen has a "short lumen rapid exchange" construction and is typically formed over the distal-most 1 cm to 10 cm of the tubular body, typically being formed over the distal-most 1 cm to 5 cm of the tubular body. The guidewire lumen will typically have its distal port located at the distal tip of the tubular body and will have a side port located proximally of the distal tip, within the distances set forth previously.

The working lumen may extend from the proximal end of the tubular body to the distal tip thereof, but will usually be terminated before reaching the distal tip. Thus, the guidewire lumen may be disposed at least partially adjacent to or parallel to the working lumen, or the guidewire lumen may be disposed proximally of and in tandem with the working lumen.

The present invention provides for the reinforcement and stiffening of the tubular body of the catheter sheath in the region of the side port of the guidewire lumen. As described previously, the provision of a side port in monorail catheter designs is problematic since it compromises the structural strength of the catheter sheath. This is a particular problem in catheter systems having an internal working shaft, where the working shaft is disposed immediately proximal to the side lumen. When such catheter systems are advanced over a guidewire through the tortuous region of a patient's vasculature, particularly when entering a side or branch blood vessel, juxtaposition of the working element and the side port will frequently cause the catheter sheath to prolapse or collapse onto the guidewire. Such collapse, in turn, can make it very difficult to further advance the catheter over the guidewire.

The present invention specifically provides a stiffening member within the tubular body adjacent the side port of the guidewire lumen. The stiffening member will provide for controlled bending of the tubular body in the region immediately distal and proximal of the side port. Typically, the stiffening member will have a length in the range from 0.25 cm to 5 cm, usually from 0.5 cm to 2 cm, and will be tapered from the middle in both the proximal and distal directions so that it provides maximum strengthening at the side port with increasing flexibility as the distance from the side port increases.

Exemplary stiffening members include tapered polymeric wedges, spring coils, tapered spring coils, flat resilient members, metal wedges, and the like. The stiffening members may be secured directly to the tubular body, frequently being fixed within the working lumen in a region adjacent the side port. In an exemplary embodiment, a tapered polymeric plug is disposed within central lumen of the tubular body to define the working lumen on its proximal side and the guidewire lumen on its distal side. Alternatively, the stiffening member may be attached to the working shaft on the distal side of the working element. In a second exemplary embodiment, the stiffening member is a tapered wire coil attached to the distal end of an ultrasonic imaging core. In some cases, it may be desirable to initialize two-component stiffening members including both a component secured within the distal working lumen and a second component attached to the working shaft.

Figure 2:
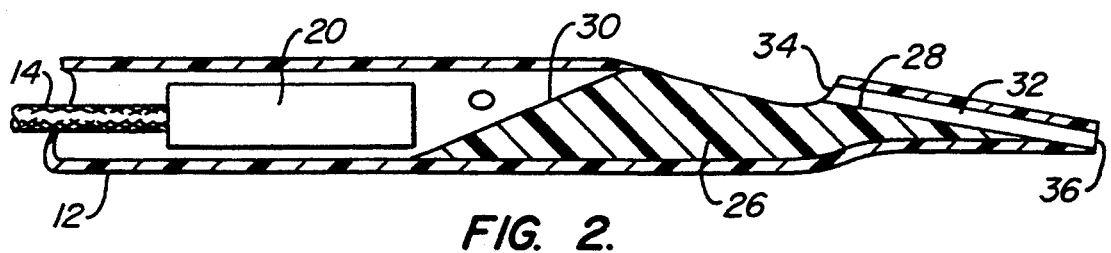
FIG. 2 is a side view of the catheter system of FIG. 1, shown in cross-section.

Referring now to the drawings, a catheter system 10 comprises a catheter sheath 12 having a rotatable working shaft 14 in a working lumen 16 thereof. The working element 14 is a rotatable imaging core having a drive spindle 18 at its proximal end. The construction and use of imaging cores for intravascular imaging is well described in the patent and medical literature, with commercial systems available from suppliers such as Cardiovascular Imaging Systems, Inc., Sunnyvale, Calif. 94086. As illustrated in FIG. 2, the working shaft 14 of the imaging core has a distal transducer housing 20 which typically includes an ultrasonic transducer mounted by itself, or in tandem with a mirror, which directs an ultrasonic signal radially outward for scanning the blood vessel as the shaft 14 is rotated.

The catheter sheath 12 comprises a tubular body which initially (prior to forming into the catheter sheath as described hereinafter) includes a single, central lumen extending from proximal end 22 to distal end 24 thereof. The catheter sheath 12 is formed by inserting a tapered polymeric wedge 26 into the distal end of the central lumen. Mandrils are used to form the wedge so that it has a distal inclined surface 28 and a proximal inclined surface 30, and the wedge may be formed from any organic polymer having the requisite flexibility and formability, such as any of the catheter body materials listed above. Usually, the distal inclined surface will be formed as part of the guidewire lumen 32 which extends from side port 34 to distal port 36, so that it may receive a guidewire GW, as shown in broken line in FIG. 1. In the embodiment of FIGS. 1 and 2, the tapered wedge 26 acts to isolate the working lumen 16 from the guidewire lumen 32. Moreover, the tapered leading (distal) edge and trailing (proximal) edge of the wedge provide the desired controlled bending, as will be described in more detail in connection with FIG. 6 hereinafter.

Figure 3:
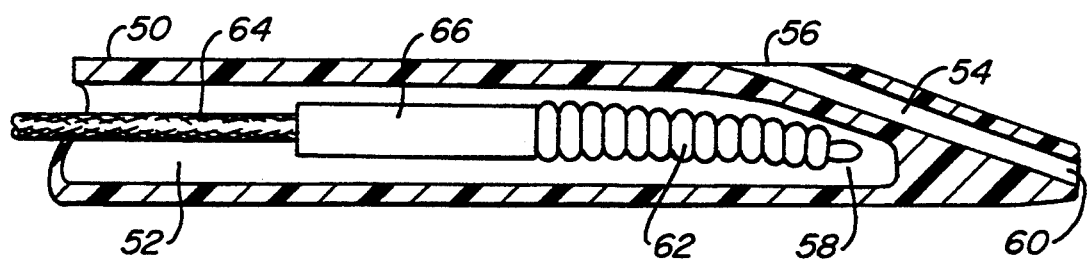
FIG. 3 is a side, cross-sectional view of an alternative embodiment of the catheter system of the present invention, employing a stiffening member attached to an imaging core.

Referring now to FIG. 3, an alternative embodiment of the catheter system and sheath of the present invention will be described. Catheter sheath 50 has a working lumen 52 and a guidewire lumen 54. In contrast with the embodiment of FIGS. 1 and 2, the working lumen 52 and guidewire lumen 54 overlap at their distal and proximal ends, respectively. Thus, side port 56 of the guidewire lumen 54 lies adjacent distal end 58 of the working lumen 52. Distal port 60 of the guidewire lumen 54 continues to be located at the distal tip of the catheter sheath 50. A stiffening member 62 (in the form of a tapered helical coil) is secured to the distal end of a working shaft 64, more particularly being shown secured to the distal end of an ultrasonic imaging assembly 66. Location of the stiffening member 62 at the distal end of the rotatable ultrasonic imaging housing 66 has additional advantages, as described generally in copending application Ser. No. 08/098,549, the full disclosure of which is incorporated herein by reference.

Figure 4:
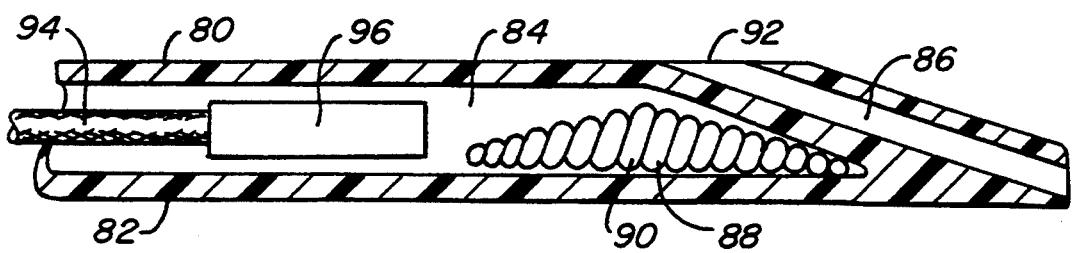
FIG. 4 illustrates an alternative embodiment of the catheter system of the present invention, employing a stiffening member attached within the distal end of a working lumen of the catheter sheath.

Referring now to FIG. 4, a third embodiment of a catheter sheath 80 constructed in accordance with the principles of the present invention will be described. Catheter sheath 80 comprises a tubular body 82 having a working lumen 84 and a guidewire lumen 86, where the working and guidewire lumens are overlapping as just described in connection with FIG. 3. Rather than having the stiffening element secured to the working element, catheter sheath 80 has a stiffening element 88 fixedly secured within the working lumen 84, preferably at its distal end. The stiffening member 88 is shown to have a doubly tapered configuration, where the stiffness is maximum near the center and decreases in both the proximal and distal directions. By locating center portion 90 directly adjacent side port 92 of the guidewire lumen, the controlled bending of the distal end of the catheter sheath 80 can be achieved. Working shaft 94 having an ultrasonic imaging assembly 96 at its distal end is mounted within the working lumen 84 and disposed proximally of the stiffening member 88. The tapered stiffening element 88 is illustrated as a doubly tapered helical coil, but could also be a polymeric wedge, a metal leaf spring, or any other resilient member capable of providing the desired flexibility profile.

Figure 4A:
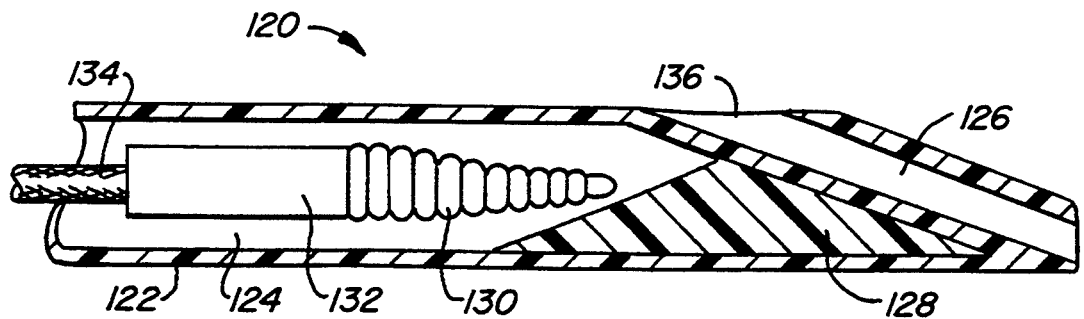
FIG. 4A illustrates a further alternative embodiment of the catheter system of the present invention, employing a two component stiffening system.

Referring now to FIG. 4A, a fourth embodiment of a catheter sheath 120 constructed in accordance with the principles of the present invention will be described. Catheter sheath 120 comprises a tubular body 122 having a working lumen 124 and a guidewire lumen 126, where the working lumen overlaps with the guidewire lumen in a manner similar to FIGS. 3 and 4. Catheter sheath 120 employs a two component stiffening system where a tapered polymeric wedge 128 is located at the distal-most end of the working lumen 124 and a separate stiffening member 130 (in the form of a tapered helical coil) is attached to the distal end of a working element 132 (in the form of an ultrasonic transducer of tandem transducer/mirror combination) on a flexible drive shaft 134. The stiffening member 130 overlaps with the tapered wedge 128, and the combination provides highly controlled bending of the catheter tip in the region of guidewire side port 136.

Figure 5:
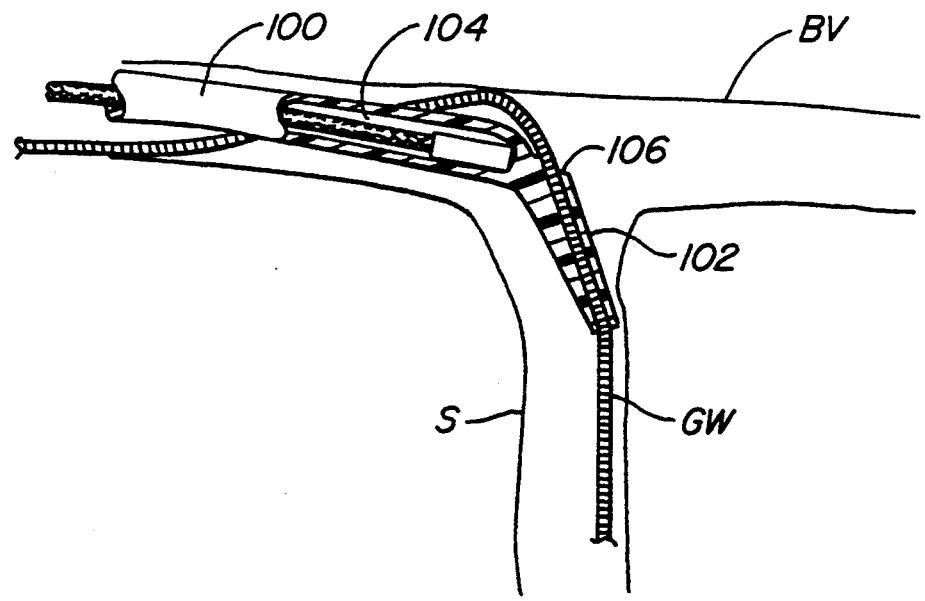
FIG. 5 illustrates the use of a prior art catheter system for introducing an imaging core over a guidewire to a branch blood vessel.

Referring now to FIG. 5, use of an exemplary prior art catheter sheath 100 in advancing from a blood vessel BV to a side or branch vessel S over a guidewire GW as illustrated. The catheter sheath 100 includes a monorail tip 102 at its distal end and a working lumen 104 disposed proximally of the guidewire lumen. As the guidewire lumen passes over the guidewire from the blood vessel BV to the side vessel S, stress will be localized at side port 106 where the guidewire passes out of the guidewire lumen 102. In the absence of reinforcement, the monorail tip of the catheter sheath 100 will bend sharply relative to the proximal portion of the catheter sheath, making further advance of the catheter sheath difficult.

Figure 6:
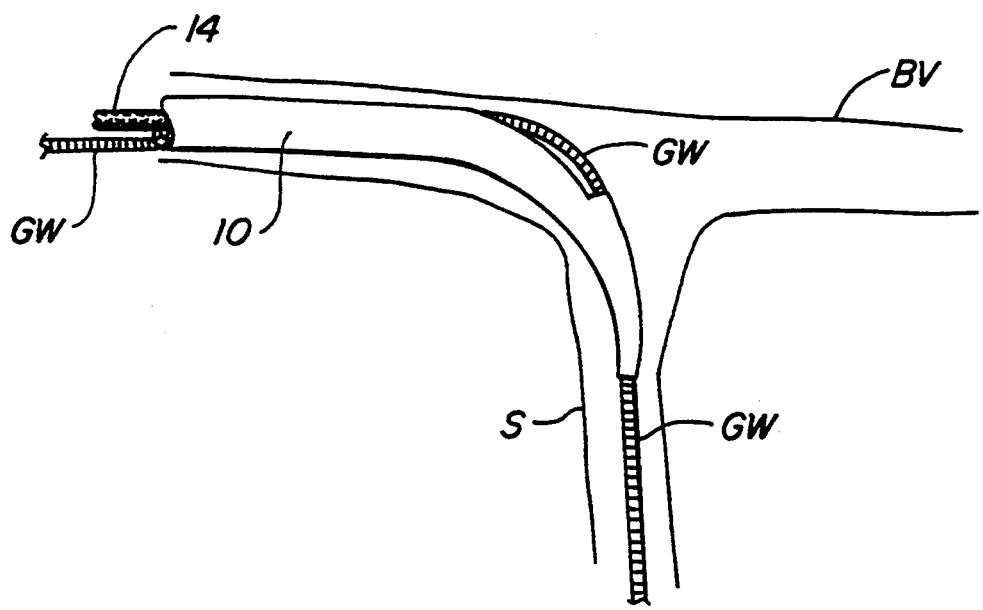
FIG. 6 illustrate use of the catheter of FIGS. 1 and 2 for introducing an imaging core over a guidewire to a branch blood vessel.

In contrast, using the catheter system 10 of the present invention, the catheter sheath 12 may be advanced over guidewire GW with its distal end bending smoothly (to define a relatively uniform arc as it follows the guidewire, as illustrated in FIG. 6. Such controlled bending can be achieved with any of the embodiments described previously.

Although the foregoing invention has been described in some detail by way of illustration and example, for purposes of clarity of understanding, it will be obvious that certain changes and modifications may be practiced within the scope of the appended claims.

What is claimed is:

1. A catheter system comprising:
   a catheter sheath including a tubular body having a proximal end, a distal end, and a working lumen and a guidewire lumen, extending therethrough wherein the guidewire lumen extends between a side port and a distal port;
   a flexible working shaft having a proximal end and a distal end, the shaft being disposed in the working lumen and having a work element attached to the shaft near the distal end of the shaft; and
   a stiffening member disposed in the working lumen, distal to the work element on the working shaft said stiffening member having a distal end and a proximal end, the distal end being located distal to the side port and the proximal end being located proximal to the side port.

2. A catheter system as in claim 1, wherein the working lumen and the guidewire lumen are isolated from each other.

3. A catheter system as in claim 2, wherein the distal end of the working lumen does not overlap with the proximal end of the guidewire lumen.

4. A catheter system as in claim 2, wherein the distal end of the working lumen overlaps with the proximal end of the guidewire lumen.

5. A catheter system as in claim 1, wherein the tubular body consists essentially of a single extrusion.

6. A catheter system as in claim 1, wherein the stiffening member is fixedly secured within the working lumen of the tubular body.

7. A catheter system as in claim 6, wherein the stiffening member is a polymeric wedge.

8. A catheter system as in claim 6, wherein the stiffening member is a wire coil.

9. A catheter system as in claim 1, wherein the stiffening member is attached to the flexible working shaft and disposed distally of the work element so that said stiffening member lies adjacent the side port when the working shaft is in place within the catheter sheath.

10. A catheter system as in claim 9, wherein the stiffening member is a wire coil.

11. A catheter system as in claim 1, wherein the stiffening member comprises a first component fixedly secured within the working lumen and a second component attached to the flexible working shaft and disposed distally of the work element.

12. A catheter sheath comprising:
    a tubular body having a proximal end, a distal end, and a working lumen and a guidewire lumen, extending therethrough wherein the guidewire lumen extends between a side port and a distal port; and
    a stiffening member secured within the working lumen near the distal end of the tubular body, the stiffening member having a proximal end that is located proximal to the side port and a distal end extending distally beyond the side port.

13. A catheter system as in claim 12, wherein the working lumen and the guidewire lumen are isolated from each other.

14. A catheter sheath as in claim 13, wherein the distal end of the working lumen does not overlap with the proximal end of the guidewire lumen.

15. A catheter sheath as in claim 13, wherein the distal end of the working lumen overlaps with the proximal end of the guidewire lumen.

16. A catheter sheath as in claim 12, wherein the tubular body consists essentially of a single extrusion.

17. A catheter sheath as in claim 12, wherein the stiffening member is fixedly secured within the working lumen of the tubular body.

18. A catheter sheath as in claim 17, wherein the stiffening member is a polymeric wedge.

19. A catheter sheath as in claim 17, wherein the stiffening member is a coil.

20. A catheter system comprising:
    a catheter sheath including a tubular body having a proximal end, a distal end, a working lumen, and a guidewire lumen, wherein the guidewire lumen extends between a side port and a distal port;
    a flexible working shaft having a proximal end and a distal end, the shaft being disposed in the working lumen and having a work element near the distal end of the shaft; and
    a wire coil adjacent the side port and distal to the work element on the working shaft, and wherein the wire coil is fixedly secured within the working lumen of the tubular body.

21. A catheter system comprising:
- a catheter sheath including a tubular body having a proximal end, a distal end, a working lumen, and a guidewire lumen, wherein the guidewire lumen extends between a side port and a distal port;
- a flexible working shaft having a proximal end and a distal end, the shaft being disposed in the working lumen and having a work element near the distal end of the shaft; and
- a wire coil adjacent the side port and distal to the work element on the working shaft, and wherein the wire is attached to the flexible working shaft and disposed distally of the work element so that said wire coil lies adjacent the side port when the working shaft is in place within the catheter sheath.

22. A catheter system comprising:
- a catheter sheath including a tubular body having a proximal end, a distal end, a working lumen, and a guidewire lumen, wherein the guidewire lumen extends between a side port and a distal port;
- a flexible shaft having a proximal end and a distal end, the shaft being disposed in the working lumen and having an ultrasonic imaging core near the distal end of the shaft; and
- a stiffening member adjacent the side port and distal to the imaging core on the working shaft.

23. A method for introducing an ultrasonic imaging catheter sheath to a blood vessel over a guidewire, comprising the steps of providing a guidewire; introducing the guidewire into the blood vessel; providing an ultrasonic imaging catheter sheath the ultrasonic imaging catheter sheath including a working lumen and a guidewire lumen and extending therethrough, wherein the guidewire lumen extends between a side port and a distal port, and the ultrasonic imaging element disposed in the working lumen, and a stiffening element secured within the working lumen of the sheath, the stiffening element having a proximal end that is proximal located to the side port and a distal end extending distally beyond the side port;

and
introducing the catheter ultrasonic imaging into the blood vessel over the guidewire, wherein prolapse of the catheter at the side port is inhibited.

24. A method as in claim 23, wherein the catheter is stiffened by fixedly securing the stiffening element within the catheter.

25. A method as in claim 23, wherein the catheter is stiffened by providing the stiffening element distally of the ultrasonic imaging element.

26. A method as in claim 23, further comprising a flexible working shaft located within the catheter, and having said ultrasonic imaging element attached thereto and wherein the catheter is stiffened by providing the stiffening element with a first component that is fixedly secured within the working lumen and a second component that is attached to the flexible working shaft distally of the imaging element.

* * * * *